United States Patent
Zhong et al.

(10) Patent No.: US 10,138,181 B2
(45) Date of Patent: Nov. 27, 2018

(54) METHOD FOR CHLORINATION AND DEHYDROGENATION OF ETHANE

(71) Applicant: ZHONGKE YIGONG (XIAMEN) CHEMICAL TECHNOLOGY CO., LTD., Xiamen, Fujian (CN)

(72) Inventors: Jingguang Zhong, Fujian (CN); Xing Liu, Fujian (CN); Xuehua Liu, Fujian (CN)

(73) Assignee: ZHONGKE YIGONG (XIAMEN) CHEMICAL TECHNOLOGY CO., LTD., Xiamen, Fujian (CN)

( * ) Notice: Subject to any disclaimer, the term of this patent is extended or adjusted under 35 U.S.C. 154(b) by 0 days.

(21) Appl. No.: 15/560,397

(22) PCT Filed: May 13, 2016

(86) PCT No.: PCT/CN2016/082022
§ 371 (c)(1),
(2) Date: Sep. 21, 2017

(87) PCT Pub. No.: WO2017/054460
PCT Pub. Date: Apr. 6, 2017

(65) Prior Publication Data
US 2018/0065902 A1 Mar. 8, 2018

(30) Foreign Application Priority Data
Sep. 29, 2015 (CN) .......................... 2015 1 0630923

(51) Int. Cl.
| | | |
|---|---|---|
| C07C 5/44 | (2006.01) | |
| C07C 17/00 | (2006.01) | |
| C07C 21/00 | (2006.01) | |
| C07C 11/04 | (2006.01) | |
| C07C 17/013 | (2006.01) | |
| C07C 19/045 | (2006.01) | |
| B01J 37/00 | (2006.01) | |
| C01B 11/00 | (2006.01) | |
| C07C 17/10 | (2006.01) | |
| C07C 17/156 | (2006.01) | |

(52) U.S. Cl.
CPC .................. *C07C 5/44* (2013.01); *B01J 37/00* (2013.01); *C01B 11/00* (2013.01); *C07C 11/04* (2013.01); *C07C 17/013* (2013.01); *C07C 17/10* (2013.01); *C07C 17/156* (2013.01); *C07C 19/045* (2013.01)

(58) Field of Classification Search
CPC ....... C07C 5/44; C07C 19/045; C07C 17/013; C07C 11/04
See application file for complete search history.

(56) References Cited

U.S. PATENT DOCUMENTS 2,140,547 A * 12/1938 Reilly .................... C07C 17/00
570/234
4,207,267 A 6/1980 Schindler

FOREIGN PATENT DOCUMENTS

| CN | 104529688 A | * | 4/2015 | ............. C07C 11/04 |
|---|---|---|---|---|
| CN | 104529688 A | | 4/2015 | |
| CN | 105016952 A | | 11/2015 | |
| CN | 105152835 A | | 12/2015 | |
| CN | 105330501 A | | 2/2016 | |

OTHER PUBLICATIONS

CN104529688A_English (Year: 2015).*
Viola et al. (Vapor pressure of aluminum chloride systems. 1. Vapor pressure and triple point of pure aluminum chloride, Journal of Chemical and Engineering Data, vol. 22, No. 4, 1977, pp. 367-370 (Year: 1977).*

* cited by examiner

*Primary Examiner* — Youngsul Jeong
(74) *Attorney, Agent, or Firm* — Novick, Kim & Lee, PLLC; Allen Xue

(57) ABSTRACT

The present invention relates to a method for chlorination and dehydrogenation of ethane, comprising: mixing and reacting a low-melting-point metal chloride with $C_2H_6$, such that the low-melting-point metal chloride is reduced to a liquid-state low-melting-point metal, and the $C_2H_6$ is chlorinated and dehydrogenized to give a mixed gas containing HCl, $C_2H_6$, $C_2H_4$, $C_2H_2$ and $C_2H_3Cl$. In the method, the low-melting-point metal chloride is used as a raw material for chlorination and dehydrogenation, and the low-melting-point metal produced after the reaction is used as an intermediate medium. The method has the characteristics of simple process, low cost and high yield. Moreover, some acetylene and vinyl chloride can be produced as by-products at the same time when the ethylene is produced, by controlling the ratio of ethane to the chloride as desired in production.

12 Claims, No Drawings

METHOD FOR CHLORINATION AND DEHYDROGENATION OF ETHANE

FIELD OF INVENTION

The present invention relates to the technical field of chemical production, and to a method for dehydrogenation of ethane, and particularly to a method for chlorination and dehydrogenation of ethane.

DESCRIPTION OF RELATED ARTS

Ethane is mainly present in, and obtained by separating from petroleum gas, natural gas, coke oven gas and petroleum pyrolysis gas. Ethane is currently most widely used in the production of ethylene, which, as a cracking raw material in the preparation of ethylene, is more economical than heavier raw materials. The method for producing ethylene with ethane mainly includes steam pyrolysis, and oxidative dehydrogenation.

Steam pyrolysis is a conventional method for producing ethylene with ethane. However, steam pyrolysis has the disadvantages of high energy consumption, low heat utilization, strict material requirement for the equipment, and high production costs. Moreover, the product also contains other heavy olefins such as propylene, butadiene and aromatic hydrocarbons, which reduces the yield of ethylene.

Compared with the steam pyrolysis process, the reaction conditions are milder in the oxidative dehydrogenation of ethane to ethylene. However, in the oxidative dehydrogenation technology, the introduction of oxygen increases the oxygen-containing by-products, and the difficulty in subsequent separation and purification, and the selectivity for and the yield of ethylene are both low. Particularly, the preparation of the catalyst used in the catalytic oxidative dehydrogenation technology is troublesome. For example, European Patent Application No. EP20030704717 discloses a method for catalytic oxidative dehydrogenation of ethane, in which at least an oxide of Mo, Te, V and Nb is associated with an element of Cu, Ta, Sn, Se, W, Ti, Fe, Co, Ni, Cr, Zr, Sb, and Bi, to prepare a catalyst for oxidative dehydrogenation of ethane through a series of procedures. In this method, the conversion per pass of ethane is 40-60%, and the yield of ethylene is 20-60%. Chinese Patent Application No. 2012100126547 provides a catalyst for oxidative dehydrogenation of ethane to ethylene at a low temperature. The catalyst comprises HCl gas as a main active ingredient and $TiO_2$ as a promoter. The main active ingredient HCl gas is mixed with the raw material gases (air and ethane) and fed to a reactor, where the reaction temperature is controlled at 440-550° C., and the yield of ethylene is 45-75%.

SUMMARY OF THE PRESENT INVENTION

In view of the technical defects existing in the prior art, the present invention provides a new method for chlorination and dehydrogenation of ethane. In the present invention, a low-melting-point metal chloride is used as a raw material for chlorination and dehydrogenation, and a low-melting-point metal produced after the reaction is used as an intermediate medium. The method has the characteristics of simple process, low cost and high yield. Moreover, some acetylene and vinyl chloride can be produced as by-products at the same time when the ethylene is produced, by controlling the ratio of ethane to the chloride as desired in production.

The present invention is accomplished through the following technical solutions.

A method for chlorination and dehydrogenation of ethane is provided, which comprises: mixing and reacting a low-melting-point metal chloride with $C_2H_6$, such that the low-melting-point metal chloride is reduced to a liquid-state low-melting-point metal, and the $C_2H_6$ is chlorinated and dehydrogenized to give a mixed gas containing HCl, $C_2H_6$, $C_2H_4$, $C_2H_2$ and $C_2H_3Cl$.

Preferably, the low-melting-point metal chloride is in a gaseous state at the reaction temperature, and can be reduced at the reaction temperature by $H_2$ to give a liquid-state low-melting-point metal and hydrogen chloride. More preferably, the low-melting-point metal chloride is $BiCl_3$ or $SnCl_2$.

Preferably, the reaction temperature is 500-800° C. More preferably, the reaction temperature is 550-650° C. The reaction temperature may be 500-600° C., 600-650° C., 650-700° C. or 700-800° C.

Preferably, the molar ratio of the element chlorine in the low-melting-point metal chloride to the $C_2H_6$ is 1-4:1.

The molar ratio of the element chlorine in the low-melting-point metal chloride to the $C_2H_6$ may be 1-2:1, 2-3:1 or 3-4:1. Preferably, the reaction time is controlled such that the conversion rate of $C_2H_6$ is up to 50-99.9%.

Controlling the reaction time such that the conversion rate of $C_2H_6$ is up to 50-99.9% is achieved through a method below. The amount of unreacted ethane is determined in the dehydrogenation tail gas collected per unit of time from which hydrogen chloride is removed, and the conversion rate of $C_2H_6$ is calculated by a formula below. If the conversion rate of $C_2H_6$ is lower than 50%, the conversion rate can be increased by extending the reaction time by reducing the flow rate of ethane. If the conversion rate of $C_2H_6$ is higher than 99.9%, the conversion rate can be decreased by reducing the reaction time by increasing the flow rate of ethane.

Conversion rate of $C_2H_6$=100%-Molar concentration of ethane in dehydrogenation tail gas from which hydrogen chloride is removed.

Preferably, the method further comprises: reacting a low-melting-point metal to obtain a low-melting-point metal chloride, and feeding back to mix and react the low-melting-point metal chloride with $C_2H_6$.

More preferably, the method for reacting a low-melting-point metal to obtain a low-melting-point metal chloride is selected from one of:

Method 1: reacting a low-melting-point metal with chlorine, to obtain a low-melting-point metal chloride;

Method 2: reacting a low-melting-point metal with oxygen or the air, to obtain a metal oxide; and absorbing the HCl obtained after the chlorination and dehydrogenation of $C_2H_6$ by the metal oxide, to obtain a low-melting-point metal chloride; and Method 3: when the low-melting-point metal chloride is $SnCl_2$, reacting the low-melting-point Sn obtained from the reduction of the $SnCl_2$ with hydrochloric acid, to obtain a low-melting-point metal chloride, that is, $SnCl_2$, and $H_2$.

Preferably, the present method further comprises the utilization of HCl in the mixed gas containing HCl, $C_2H_6$, $C_2H_4$, $C_2H_2$, and $C_2H_3Cl$ through any one of:

Method 1: absorbing the HCl with water to produce a hydrochloric acid product;

Method 2: applying HCl in the oxidation and chlorination of $C_2H_4$ to obtain a dichloroethane product; and Method 3: catalytically oxidizing HCl with oxygen or the air into $Cl_2$, and feeding back to react with a low-melting-point metal, to obtain a low-melting-point metal chloride.

Preferably, the mixed gas from which the HCl is separated is further separated to obtain a $C_2H_4$, a $C_2H_2$, and a $C_2H_3Cl$ product respectively. The mixed gas from which the HCl is separated may be further separated through a conventional method such as rectification to obtain a $C_2H_4$, a $C_2H_2$, and a $C_2H_3Cl$ product respectively. The fundamental principle underlying the method for chlorination and dehydrogenation of ethane according to the present invention is as follows:

     (1)

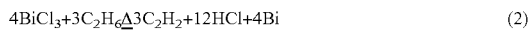     (2)

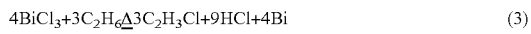     (3)

or

     (1)

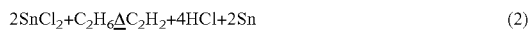     (2)

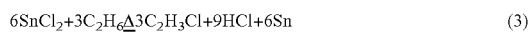     (3)

The present invention has at least one of the following beneficial effects:

(1) A low-melting-point metal chloride is used as a dehydrogenation material for chlorination and dehydrogenation of ethane by a gas phase reaction. The reaction rate is fast, the efficiency is high, and the reaction can be completed instantaneously in several seconds. Therefore, the method is suitable for use in massive industrial production.

(2) The reaction intermediate is a liquid-state low-melting-point metal, which is easy for transport and separation, and the reaction device is simple and practicable.

(3) Different proportions of $C_2H_4$, $C_2H_2$, and $C_2H_3Cl$ can be obtained by controlling the conversion rate of $C_2H_6$ per pass. The conversion rate of $C_2H_6$ per pass can be up to 98% or higher. When ethylene is a target product, the selectivity for ethylene can be up to 95% or higher. When deep dehydrogenation is employed, 10% or higher of $C_2H_2$ or $C_2H_3Cl$ can be obtained. Thus, the present method is an effective method for directly synthesizing $C_2H_3Cl$.

(4) The heat generated during the metal oxidation and chlorination can be directly used in the vaporization of the chloride and the dehydrogenation of ethane, whereby the energy is saved.

DETAILED DESCRIPTION OF THE PREFERRED EMBODIMENTS

The technical solutions of the present invention will now be described by way of specific examples. It is to be understood that one or more process steps mentioned in the present invention do not exclude the presence of other process steps before or after the combined steps, or other process steps may be added between these explicitly mentioned steps. It is to be understood that these examples are merely illustrative of the present invention and are not intended to limit the scope of the present invention. Unless otherwise specified, the numbering of each process step is only a convenient means of identifying the process steps, rather than limiting the order of the process steps or limiting the scope of the present invention to be implemented, and the change or adjustment made to the relative relationship therebetween without substantially changing the technical content is contemplated in the scope of the invention to be implemented.

Example 1

(1) The $BiCl_3$ vapor was mixed with $C_2H_6$, and the reaction time was controlled, such that the conversion rate of $C_2H_6$ was 50%. The molar ratio of the element chlorine in $BiCl_3$ to the $C_2H_6$ was 1:1, and the reaction temperature was 500° C. The $C_2H_6$ was chlorinated and dehydrogenized to give a mixed gas containing HCl, $C_2H_6$, $C_2H_4$, $C_2H_2$, and $C_2H_3Cl$, and $BiCl_3$ was reduced to liquid-state Bi.

(2) Chlorine was bubbled through the metal Bi melt obtained in the step 1), to convert Bi into $BiCl_3$ for continuous reaction with ethane.

(3) The HCl in the mixed gas containing HCl, $C_2H_6$, $C_2H_4$, $C_2H_2$ and $C_2H_3Cl$ obtained in the step 1) was absorbed with water, to obtain a mixed gas containing $C_2H_6$, $C_2H_4$, $C_2H_2$, and $C_2H_3Cl$, etc., and a by-product hydrochloric acid. The main ingredients in the HCl removed tail gas obtained from chlorination and dehydrogenation of ethane are shown in Table 1.

TABLE 1

Main ingredients in the gaseous phase in the HCl removed tail gas obtained from chlorination and dehydrogenation of ethane in Example 1

| Component | Retention time (min) | Peak area | Peak height | Molar concentration (%) |
|---|---|---|---|---|
| Methane | 0.86 | 9666 | 7364 | 0.023 |
| Ethane | 1.04 | 20614375 | 14146103 | 48.38 |
| Ethylene | 1.13 | 21798544 | 13254713 | 51.16 |
| Acetylene | 1.46 | 185413 | 116140 | 0.44 |
| Chloroethylene | 5.01 | 2260 | 140 | 0.0053 |
| In total | | 42610258 | 27524460 | 100.01 |

Example 2

(1) The $BiCl_3$ vapor was mixed with $C_2H_6$, and the reaction time was controlled, such that the conversion rate of $C_2H_6$ was 74%. The molar ratio of the element chlorine in $BiCl_3$ to the $C_2H_6$ was controlled to 2:1, and the reaction temperature was 600° C. The $C_2H_6$ was chlorinated and dehydrogenized to give a mixed gas containing HCl, $C_2H_6$, $C_2H_4$, $C_2H_2$, and $C_2H_3Cl$, and $BiCl_3$ was reduced to liquid-state Bi.

(2) Oxygen was bubbled through the metal Bi melt obtained in the step 1), to convert Bi into $Bi_2O_3$, and the HCl obtained in the step (1) was absorbed by the $Bi_2O_3$ subsequently to obtain $BiCl_3$ for continuous reaction with ethane.

(3) The HCl in the mixed gas containing HCl, $C_2H_6$, $C_2H_4$, $C_2H_2$ and $C_2H_3Cl$ obtained in the step 1) was absorbed by the $Bi_2O_3$ layer, to obtain a mixed gas containing $C_2H_6$, $C_2H_4$, $C_2H_2$, and $C_2H_3Cl$, etc. The main ingredients in the HCl removed tail gas obtained from chlorination and dehydrogenation of ethane are shown in Table 2.

TABLE 2

Main ingredients in the gaseous phase in the
HCl removed tail gas obtained from chlorination
and dehydrogenation of ethane in Example 2

| Component | Retention time (min) | Peak area | Peak height | Molar concentration (%) |
|---|---|---|---|---|
| Methane | 0.85 | 184217 | 134826 | 0.45 |
| Ethane | 1.03 | 10747164 | 7560033 | 26.16 |
| Ethylene | 1.12 | 29432421 | 16559447 | 71.40 |
| Acetylene | 1.45 | 424604 | 261458 | 1.03 |
| Chloroethylene | 5.04 | 369146 | 692598 | 0.92 |
| In total | | 41157554 | 24463623 | 99.96 |

Example 3

(1) The $BiCl_3$ vapor was mixed with $C_2H_6$, and the reaction time was controlled, such that the conversion rate of $C_2H_6$ was 97%. The molar ratio of the element chlorine in $BiCl_3$ to the $C_2H_6$ was 3:1, and the reaction temperature was 650° C. The $C_2H_6$ was chlorinated and dehydrogenized to give a mixed gas containing HCl, $C_2H_6$, $C_2H_4$, $C_2H_2$, and $C_2H_3Cl$, and $BiCl_3$ was reduced to liquid-state Bi.

(2) Chlorine was bubbled through the metal Bi melt obtained in the step 1), to convert Bi into $BiCl_3$ for continuous reaction with ethane.

(3) The HCl in the mixed gas containing HCl, $C_2H_6$, $C_2H_4$, $C_2H_2$ and $C_2H_3Cl$ obtained in the step 1) was absorbed with water, to obtain a mixed gas containing $C_2H_6$, $C_2H_4$, $C_2H_2$, and $C_2H_3Cl$, etc., and a by-product hydrochloric acid. The main ingredients in the HCl removed tail gas obtained from chlorination and dehydrogenation of ethane are shown in Table 3.

TABLE 3

Main ingredients in the gaseous phase in the
HCl removed tail gas obtained from chlorination
and dehydrogenation of ethane in Example 3

| Component | Retention time (min) | Peak area | Peak height | Molar concentration (%) |
|---|---|---|---|---|
| Methane | 0.86 | 532721 | 407419 | 1.31 |
| Ethane | 1.05 | 1053504 | 785805 | 2.61 |
| Ethylene | 1.13 | 34063085 | 18044507 | 83.96 |
| Acetylene | 1.45 | 3108821 | 1846049 | 7.68 |
| Chloroethylene | 4.96 | 1805211 | 322805 | 4.46 |
| In total | | 40563342 | 21406585 | 100.02 |

Example 4

(1) The $BiCl_3$ vapor was mixed with $C_2H_6$, and the reaction time was controlled, such that the conversion rate of $C_2H_6$ was 98%. The molar ratio of the element chlorine in $BiCl_3$ to the $C_2H_6$ was 4:1, and the reaction temperature was 700° C. The $C_2H_6$ was chlorinated and dehydrogenized to give a mixed gas containing HCl, $C_2H_6$, $C_2H_4$, $C_2H_2$, and $C_2H_3Cl$, and $BiCl_3$ was reduced to liquid-state Bi.

(2) Oxygen was bubbled through the metal Bi melt obtained in the step 1), to convert Bi into $Bi_2O_3$, and the HCl obtained in the step (1) was absorbed by the $Bi_2O_3$ subsequently, to obtain $BiCl_3$ for continuous reaction with ethane.

(3) The HCl in the mixed gas containing HCl, $C_2H_6$, $C_2H_4$, $C_2H_2$ and $C_2H_3Cl$ obtained in the step 1) was absorbed by the $Bi_2O_3$ layer, to obtain a mixed gas containing $C_2H_6$, $C_2H_4$, $C_2H_2$, and $C_2H_3Cl$, etc. The main ingredients in the HCl removed tail gas obtained from chlorination and dehydrogenation of ethane are shown in Table 4.

TABLE 4

Main ingredients in the gaseous phase in the
HCl removed tail gas obtained from chlorination
and dehydrogenation of ethane in Example 4

| Component | Retention time (min) | Peak area | Peak height | Molar concentration (%) |
|---|---|---|---|---|
| Methane | 0.86 | 532055 | 412012 | 1.31 |
| Ethane | 1.05 | 618220 | 468862 | 1.53 |
| Ethylene | 1.13 | 30433728 | 16630354 | 75.12 |
| Acetylene | 1.45 | 6019903 | 3423861 | 14.86 |
| Chloroethylene | 4.94 | 2879373 | 471988 | 7.11 |
| In total | | 40483279 | 17983216 | 99.90 |

Example 5

(1) The $SnCl_2$ vapor was mixed with $C_2H_6$, and the reaction time was controlled, such that the conversion rate of $C_2H_6$ was 77%. The molar ratio of the element chlorine in $SnCl_2$ to the $C_2H_6$ was 2:1, and the reaction temperature was 800° C. The $C_2H_6$ was chlorinated and dehydrogenized to give a mixed gas containing HCl, $C_2H_6$, $C_2H_4$, $C_2H_2$, and $C_2H_3Cl$, and $SnCl_2$ was reduced to liquid-state Sn.

(2) The metal Sn obtained in the step 1) was reacted with hydrochloric acid obtained subsequent to the step 1), to obtain $SnCl_2$ for continuous reaction with ethane.

(3) The HCl in the mixed gas containing HCl, $C_2H_6$, $C_2H_4$, $C_2H_2$ and $C_2H_3Cl$ obtained in the step 1) was absorbed with water, to obtain a mixed gas containing $C_2H_6$, $C_2H_4$, $C_2H_2$, and $C_2H_3Cl$, etc., and a by-product hydrochloric acid. The main ingredients in the HCl removed tail gas obtained from chlorination and dehydrogenation of ethane are shown in Table 5.

TABLE 5

Main ingredients in the gaseous phase in the
HCl removed tail gas obtained from chlorination
and dehydrogenation of ethane in Example 5.

| Component | Retention time (min) | Peak area | Peak height | Molar concentration (%) |
|---|---|---|---|---|
| Methane | 0.86 | 1681688 | 1111058 | 5.99 |
| Ethane | 1.05 | 6545196 | 4367150 | 23.24 |
| Ethylene | 1.14 | 19506153 | 10995253 | 69.07 |
| Acetylene | 1.47 | 405920 | 235319 | 1.46 |
| Chloroethylene | 4.94 | 39475 | 3749 | 0.14 |
| In total | | 28178432 | 16712529 | 99.90 |

The foregoing descriptions are merely preferred embodiments of the present invention, which are not intended to limit the present invention in any way. It should be noted that modifications and supplements may be made by those of ordinary skill in the art without departing from the spirit of the present invention, which are contemplated in the scope of the present invention. Various changes, modifications and evolved equivalent variations may be made to the disclosure of the present invention by those skilled in the art without departing from the spirit and scope of the present invention, which constitute equivalent embodiments of the present invention. Any equivalent changes, modifications and evolutions made to the embodiments in accordance with the essential technical aspects of the present invention fall within the scope of the present invention.

What is claimed is:

1. A method for chlorination and dehydrogenation of ethane, comprising:
   mixing a low-melting-point metal chloride in a gas phase with $C_2H_6$ at a reaction temperature;
   reducing the low-melting-point metal chloride to form a liquid-state low-melting-point metal; and
   chlorinating and dehydrogenizing the $C_2H_6$ to produce a mixed gas containing HCl, $C_2H_6$, $C_2H_4$, $C_2H_2$, and $C_2H_3Cl$.

2. The method of according to claim 1, wherein the low-melting-point metal chloride is $BiCl_3$ or $SnCl_2$.

3. The method of claim 1, wherein the reaction temperature is 500-800° C.

4. The method of claim 1, wherein a molar ratio of chlorine in the low-melting-point metal chloride to the $C_2H_6$ is from 1:1 to 4:1.

5. The method of claim 1, further comprising controlling a reaction time so that a conversion rate of $C_2H_6$ is up to 50-99.9 wt %.

6. The method of claim 1, further comprising: reacting a low-melting-point metal with a chlorine source to obtain the low-melting-point metal chloride, and mixing the low-melting-point metal chloride in the gas phase with the $C_2H_6$.

7. The method of claim 1, further comprising:
   reacting the low-melting-point metal with oxygen or air to obtain a metal oxide; and
   reacting the metal oxide with a chlorine source to obtain the low-melting-point metal chloride.

8. The method of claim 1, further comprising: absorbing HCl in the mixed gas containing HCl, $C_2H_6$, $C_2H_4$, $C_2H_2$, and $C_2H_3Cl$ with water to produce a hydrochloric acid product.

9. The method of claim 8, wherein the mixed gas after a separation of HCl is further separated to obtain a $C_2H_4$ product, a $C_2H_2$ product, and a $C_2H_3Cl$ product.

10. The method of claim 7, wherein the chlorine source comprises HCl separated from the mixed gas containing HCl, $C_2H_6$, $C_2H_4$, $C_2H_2$, and $C_2H_3Cl$.

11. The method of claim 6, wherein the low-melting-point metal is Sn, the low-melting-point metal chloride is $SnCl_2$, and the chlorine source is hydrochloric acid.

12. The method of claim 1, wherein the liquid-state low-melting-point metal is the low-melting-point metal in a molten state.

* * * * *